(12) United States Patent
Schwarz et al.

(10) Patent No.: US 10,315,253 B2
(45) Date of Patent: Jun. 11, 2019

(54) MOULD, METHOD FOR PRODUCING A GREEN COMPACT AND USE OF THE MOULD

(71) Applicant: CERATIZIT AUSTRIA GMBH, Reutte (AT)

(72) Inventors: Gerhard Schwarz, Ehrwald (AT); Alexander Singer-Schnoeller, Weissenbach (AT); Christoph Wetzel, Pinswang (AT)

(73) Assignee: CERATIZIT Austria Gesellschaft m.b.H., Reutte (AT)

( * ) Notice: Subject to any disclaimer, the term of this patent is extended or adjusted under 35 U.S.C. 154(b) by 315 days.

(21) Appl. No.: 15/119,562

(22) PCT Filed: Feb. 13, 2015

(86) PCT No.: PCT/AT2015/000025
§ 371 (c)(1),
(2) Date: Aug. 17, 2016

(87) PCT Pub. No.: WO2015/120496
PCT Pub. Date: Aug. 20, 2015

(65) Prior Publication Data
US 2017/0246687 A1 Aug. 31, 2017

(30) Foreign Application Priority Data
Feb. 17, 2014 (AT) .................................. GM68/2014

(51) Int. Cl.
*A61F 7/00* (2006.01)
*A61F 7/10* (2006.01)
(Continued)

(52) U.S. Cl.
CPC .................. *B22F 3/16* (2013.01); *A61F 7/10* (2013.01); *B22F 3/03* (2013.01); *B30B 11/004* (2013.01);
(Continued)

(58) Field of Classification Search
None
See application file for complete search history.

(56) References Cited

U.S. PATENT DOCUMENTS 6,553,667 B1 * 4/2003 West ........................ A44C 9/00
164/80
6,582,651 B1 * 6/2003 Cochran, Jr. ........... B22F 3/001
419/36
(Continued)

FOREIGN PATENT DOCUMENTS

| JP | H07266091 A | 10/1995 |
|---|---|---|
| JP | H1094899 A | 4/1998 |

(Continued)

*Primary Examiner* — Anthony J Zimmer
(74) *Attorney, Agent, or Firm* — Laurence A. Greenberg; Werner H. Stemer; Ralph E. Locher (57) ABSTRACT

A mold for producing a green compact using powder metallurgy processes has an upper punch and a lower punch which are movable along a common press axis and a die body with a charging chute for receiving powder material. The die body has an upper region in which the upper punch is movably guided along the press axis in the charging chute, and a lower region in which the lower punch is movably guided along the press axis in the charging chute. Two cross slides realize a forming region which determines the lateral outside contour of the green compact, and are arranged on the die body so as to be displaceable in a direction which deviates from the press axis. The two cross slides only move into contact with one another when the two cross slides are arranged in their respective end position.

12 Claims, 4 Drawing Sheets

(51) Int. Cl.
*B22F 3/03* (2006.01)
*B22F 3/16* (2006.01)
*B22F 5/00* (2006.01)
*F25D 3/08* (2006.01)
*B30B 11/00* (2006.01)
*B30B 15/00* (2006.01)
*B30B 15/02* (2006.01)
*B30B 15/30* (2006.01)

(52) U.S. Cl.
CPC ........ *B30B 11/007* (2013.01); *B30B 15/0082* (2013.01); *B30B 15/022* (2013.01); *B30B 15/302* (2013.01); *F25D 3/08* (2013.01); *A61F 2007/0095* (2013.01); *B22F 2003/031* (2013.01); *B22F 2005/001* (2013.01); *B22F 2998/10* (2013.01); *F25D 2303/0822* (2013.01); *F25D 2331/8014* (2013.01)

(56) References Cited

U.S. PATENT DOCUMENTS

| | | |
|---|---|---|
| 2009/0136776 A1 | 5/2009 | Gubanich et al. |
| 2009/0257904 A1* | 10/2009 | Lawcock .................. B22F 3/03 419/66 |
| 2010/0159051 A1 | 6/2010 | Gubanich et al. |
| 2012/0003443 A1 | 1/2012 | Gubanich et al. |
| 2013/0039798 A1 | 2/2013 | Satran et al. |

FOREIGN PATENT DOCUMENTS

| | | |
|---|---|---|
| JP | H11300497 A | 11/1999 |
| WO | 2013024473 A1 | 2/2013 |

* cited by examiner

MOULD, METHOD FOR PRODUCING A GREEN COMPACT AND USE OF THE MOULD

BACKGROUND OF THE INVENTION

Field of the Invention:

The invention relates to a mould for producing a green compact using powder metallurgy processes, to a method for producing a green compact and to the use of the mould.

JP 11-300497 A discloses a moulding device for producing green compacts made of powder material. A die comprises a continuous opening in which the upper punch and a lower punch are displaceably guided along a press axis. The lateral outside contour of a green compact is determined by the die opening. Two forming punches are movably guided in the die at right angles to the press axis in order to realize an undercut in the form of a circumferential groove on the lateral outside contour of the green compact.

BRIEF SUMMARY OF THE INVENTION

It is the object of the invention to provide an improved mould and method for producing green compacts using powder metallurgy processes.

Said object is achieved with the features of the independent claims.

Advantageous developments are the object of the subclaims.

According to the main apparatus claim, a mould is prepared for producing a green compact using powder metallurgy processes. By means of the mould, powder material can be pressed to form a green compact which is then sintered in a sintering operation. For example, the mould can be used to produce green compacts for a cutting insert for machining a workpiece.

A die body of the mould comprises a charging chute in order to receive powder material. For example, the cross section of the charging chute corresponds to the contour of a green compact to be pressed in the direction of the press axis or in top view. An upper punch and a lower punch are movable along a common press axis, the upper punch being movably guided in an upper region of the die body in the charging chute and the lower punch being movably guided in a lower region of the die body in the charging chute. Thus, once the powder has been filled into the charging chute, pressure can be exerted onto the powder material arranged between the punches in order to press the powder material to form a green compact.

The mould additionally comprises at least two cross slides which together realize a forming region which determines the lateral outside contour of a green compact. The at least two cross slides are arranged on and/or in the die body so as to be displaceable in a transverse direction that deviates from the press axis. For example, the die body comprises at least two through bores or openings in which in each case one of the at least two cross slides is displaceably guided. The at least two cross slides, in particular two adjacent cross slides, only abut against one another or contact one another when the at least two cross slides are arranged in their respective end positions. A cavity which determines the (final) shape of a pressed green compact is realized in a closed state of the mould by the upper punch, the lower punch and the at least two cross slides which are arranged in their respective end positions.

To produce a green compact, the at least two cross slides, for example, are moved from an open position into a closed position or end position such that the at least two cross slides establish the outside contour of the green compact. Powder material is then filled into the die body by means of the charging chute and the filled powder material is compacted as a result of moving the upper and lower punches along the press axis until the upper and lower punches are also situated in their respective end positions. For example, the at least two cross slides are displaceable radially with respect to the press axis or at any other angle with respect to the press axis such that as a result of moving the cross slides into an open position a pressed green compact is released.

The at least two cross slides are realized such that they determine the entire lateral outside contour of a green compact or the at least two cross slides comprise all the forming faces which determine the entire lateral outside periphery of a green compact. For example, each cross slide comprises a forming portion or a forming face, the forming portions or forming faces of all the cross slides together establishing the entire lateral outside contour of a green compact. The term 'lateral outside contour' refers to all the faces that are radially offset or lie 'laterally' with respect to the press axis or the lateral outside contour includes all the outside faces of a green compact which are not established by the upper punch or lower punch.

In summary, the die does not comprise any form-giving regions or faces for producing a green compact or the die is not part of the above-described cavity which establishes the end form or outside contour of a pressed green compact. In particular, the upper die region and the lower die region are free of portions which determine the outside contour of a green compact such that no part or region of the die body determines the outside contour of a green compact.

In the case of JP 11-300497 A, the die body does comprise form-giving regions. In contrast to this, with the above-described mould the pressing region or the form-giving region, which is established by the cross slides and the upper and lower punch, is separates from the powder charging region or from the die body. As a result of the functional separation between the pressing region and the powder charging region, individual form-giving elements, for example, can be exchanged or replaced in a simple manner without the (solid) die body having to be replaced. If, for example, the lateral outside contour of a green compact is to be modified or the form-giving face (on one or several cross slides) is worn, it is only necessary to exchange one or several of the cross slides.

For example, a compact, non-divided die body with a charging chute can be prepared in which the form-giving parts are guided as described above.

In order to provide a particularly sturdy die body, the die body can be produced, for example, from several elements which are connected together in a non-releasable manner, such as, for example, from a hard metal core with a shrunk-on steel casing. For example, the at least two openings in the die body for the at least two cross slides can be realized with a rectangular cross section in order to provide simple and cost-efficient manufacturing of the cross slides.

In a preferred manner, the height of the at least two cross slides or the extension thereof in the direction of the press axis corresponds to the finished height or to the final dimension of a green compact to be pressed. In particular, the at least two cross slides are arranged between the upper region and the lower region of the die body and the height of the at least two cross slides in the direction of the press axis corresponds to the finished height of a green compact to be pressed. In said development, the extension of the breakthroughs or openings in the die body for the respective cross slides is minimized such that the (solid) die body is not weakened or is hardly weakened by the openings for the cross slides. This means that the forces occurring during the pressing operation are able to be conducted away via the die body in a reliable manner.

In a particularly preferred manner, the upper region of the die body engages around the upper punch completely in the circumferential direction such that reliable guiding of the punch in the die body is ensured. In addition to this or as an alternative to it, the lower region of the die body engages around the lower punch completely in the circumferential direction.

The upper region is preferably connected to the lower region of the die body in a fixed or non-releasable manner such that a single-part or non-divided die body is provided which withstands the forces occurring during a pressing operation in a reliable manner.

In a preferred manner, each of the at least two cross slides comprises a contact face which only moves into contact with a contact face of an adjacent cross slide when both adjacent cross sides are arranged in their end position. In an open position of the mould and during the movement into the above-described closed position, the contact faces of the at least two cross slides do not abut against one another. In particular, contact faces of adjacent cross slides do not slide along on one another. This avoids wear on the contact faces, e.g. as a result of powder particles becoming jammed between the contact faces.

Each cross slide preferably comprises two contact faces which are arranged laterally with respect to (opposite) the forming face or the forming region of the cross slide such that with the mould closed in each case the contact faces of adjacent cross slides or of cross slides that are arranged side by side contact one another. Through the contact faces that are arranged laterally with respect to the forming region, each cross slide projects laterally beyond a green compact or mould cavity or each cross slide is realized wider than its respective forming portion in a plane perpendicular to the press axis. The contact faces ensure that the cross slides abut against one another securely in the end position and the powder material or the green compact is held securely in the cavity during a pressing operation.

In a particularly preferred manner, an angle between the direction of displacement of a cross slide and the contact face of the same cross slide is at least 40° and is preferably between 45° and 90°. For example, a mould comprises two cross slides which establish the entire outside periphery of a green compact. When the two cross slides are arranged opposite the press axis and are displaceable radially to the press axis along a common (transverse) axis, the above-described angle between the contact face of one cross slide and its direction of displacement is then 90°. The angle between the direction of displacement and the contact face of an adjacent cross slide comprises the same amount such that when the two cross slides are moved together the contact faces abut against one another in a flat manner. According to an alternative development, a mould can be provided with four cross slides which are arranged in each case offset by 90° around the press axis and are radially displaceable. The angle between a contact face of a cross slide and its radial direction of displacement is then 45°. As described above, the adjacent cross slides comprise the same angle between the direction of displacement and the contact face such that with the mould closed the adjacent contact faces abut against one another. According to a further example, a mould comprises three cross slides where the angle between the contact face and the direction of displacement is 60°.

According to a further development, the contact faces are profiled or the contact faces comprise profile geometry such that the profile of adjacent contact faces engage in one another in the end position of the respective cross slides. As a result of a profiling, for example toothing, the end position of the cross slides can be additionally secured.

A method for producing a powder-metallurgical component is explained below as an example. In a first step a green compact made from a powder material is pressed using a mould as described above and the pressed green compact is then sintered such that a sintered component is created.

The pressing process preferably comprises the following steps: Prepare the mould, the upper punch, the lower punch and the at least two cross slides being arranged in a start position or open position (moved apart from one another). The lower punch can already be arranged in its end position in the open position. The at least two cross slides are moved into their respective end position such that the contact faces of adjacent cross slides do not abut against one another until the end positions have been reached. As described above, the at least two cross slides realize the forming region for the entire lateral outside contour of the green compact to be pressed. The powder material is then filled into the charging chute of the die body. In order to press the powder material between the two punches to form a green compact, the upper punch and, as an option, the lower punch are moved along the press axis until the upper punch (and lower punch) reaches its end position.

To eject the green compact out of the mould, the at least two cross slides can be moved away radially or moved into their open position such that the green compact is still held between the upper and lower punch. As a result of moving the upper and lower punch together upward or downward, the green compact can then be moved out of the die body in order then to be sintered. As an option, the method comprises the step of grinding and/or coating the sintered component.

Once a green compact has been ejected, the mould is preferably cleaned of any powder residue possibly remaining in order to ensure a fault-free pressing operation. In particular, the guide faces (for the cross slides and the punches) and the contact faces. Small bores which, for example, open out on the guide faces and by means of which a flushing medium can be conducted in order to release the faces from contaminants, are mounted, for example, in the die body. For example compressed air can be used as a flushing medium. As an alternative to this or in addition to it, the cleaning operation can be effected or supported by means of brushes. To this end, a cleaning channel can be provided in the die body, through which a brush can be guided in order, in this way, for example, to clean the contact faces of the cross slides in the installed state. In addition to this or as an alternative to it, suction devices, which suck the (released) powder residue out of the mould, can be mounted on the mould. For example, by means of the openings or bores in the die body as described above. For example, powder residues can be released from the faces by means of one or several brushes and then sucked up out of the mould by means of a suction device.

BRIEF DESCRIPTION OF THE SEVERAL VIEWS OF THE DRAWING

Exemplary embodiments of the invention are explained in more detail by way the Figures, in which.

DESCRIPTION OF THE INVENTION

Two developments of a mould for producing a green compact using powder metallurgy processes or for pressing a green compact are described below. A mould 2 with two cross slides 10a-b which are located opposite the press axis A is shown schematically in FIGS. 1a-b, 2a-b and 3a-b. A mould 2' according to an alternative development with three cross slides 10c-e is shown schematically in FIG. 4. Insofar as nothing to the contrary is stated, the elements described below, the use of the mould and the method for producing a green compact of the two developments are interchangeable with one another in an arbitrary manner. In particular, where required or depending on the shape of the green compact that can be produced therewith, more than three cross slides can be provided for a mould.

Figure 1A:
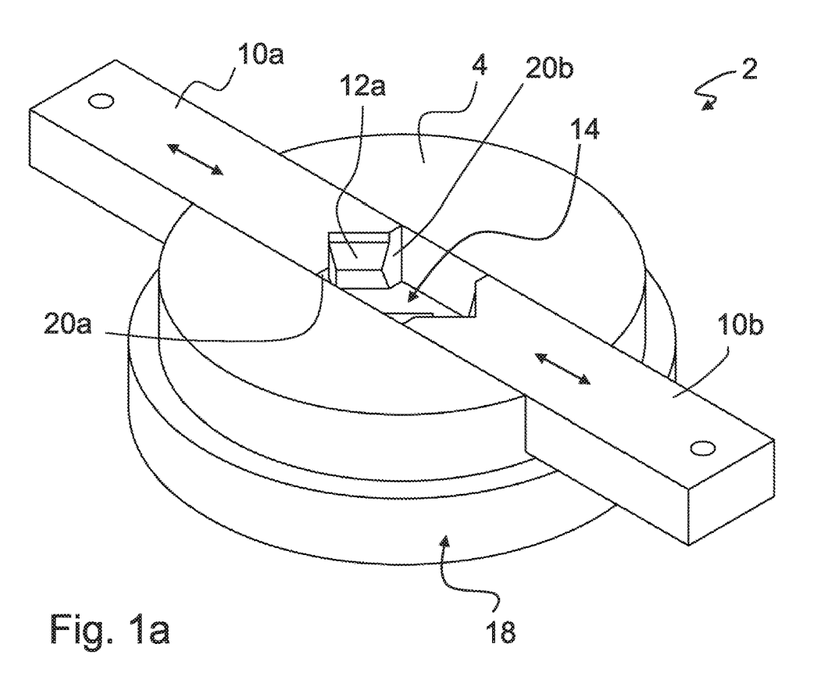
FIG. 1a-b show perspective views of a schematically represented mould with two cross slides in the open position (FIG. 1a) and closed position (FIG. 1b)
Figure 1B:
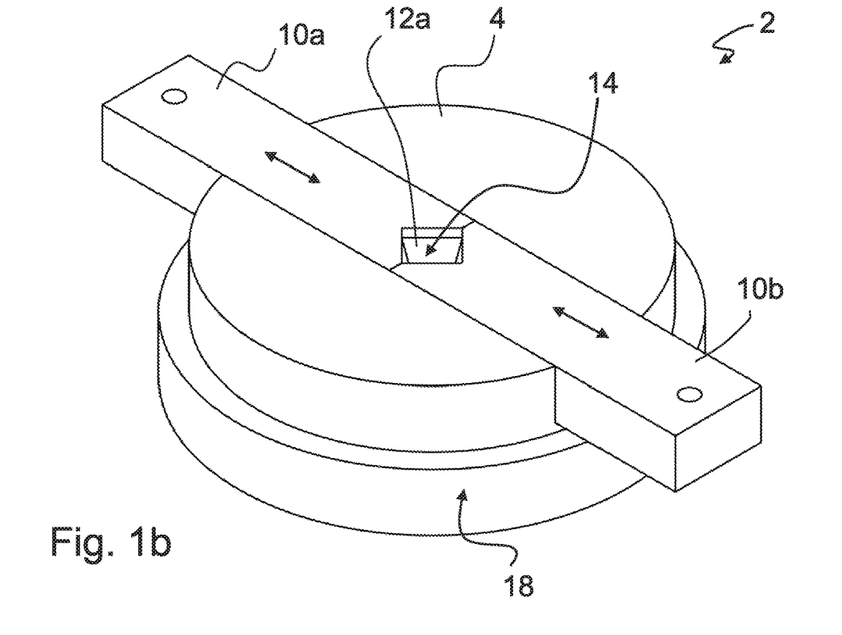

FIG. 1a-b show lateral perspective views of a mould according to a first development. FIG. 1a shows the mould 2 in the open position and FIG. 1b shows the mould 2 in the closed position. As is shown schematically in the lateral sectioned views of FIG. 2a and FIG. 3a, the mould 2 comprises a non-divided die 4 having a charging chute 14, two cross slides 10a-b and an upper punch 8 and a lower punch 6.

In order to show the different positions of the cross slides 10a-b, FIG. 1a-b, FIG. 2b and FIG. 3b do not show an upper die region 16 or the upper punch 8.

Figure 2A:
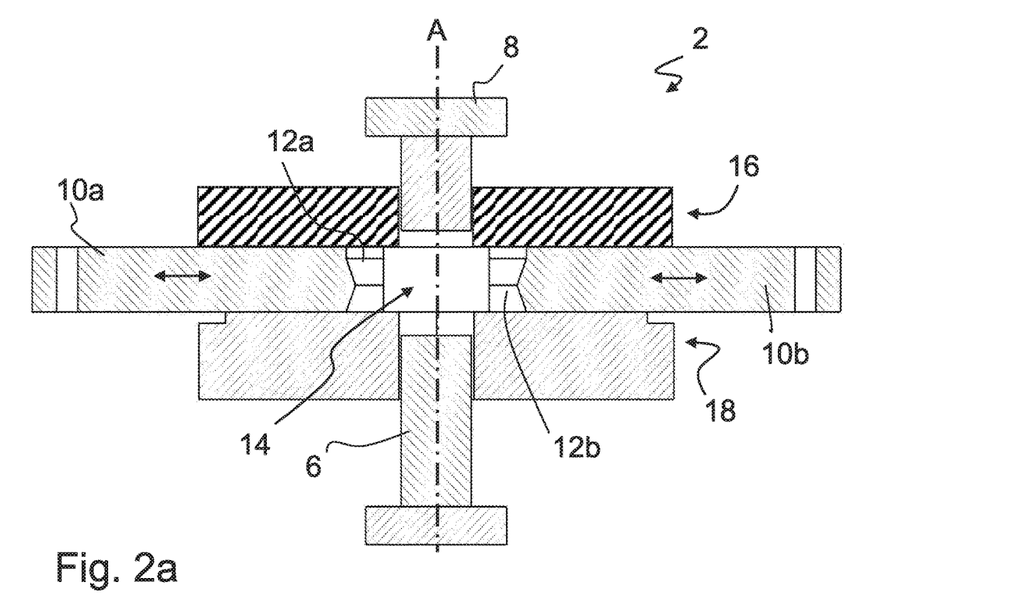
FIG. 2a-b show a sectioned side view and a top view of the mould of FIG. 1a-b in the open position.
Figure 2B:
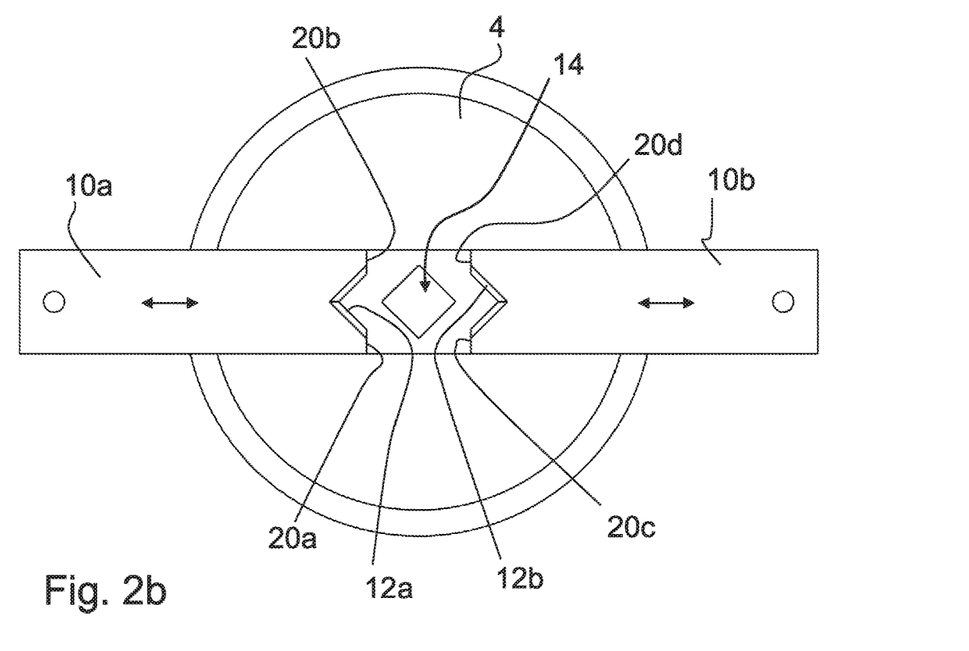
Figure 3A:
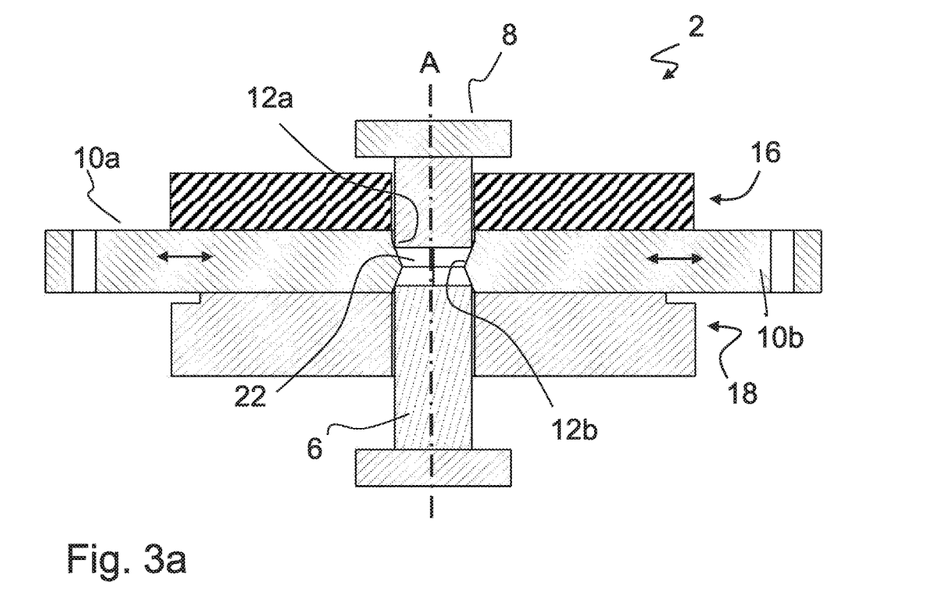
FIG. 3a-b show a sectioned side view and a top view of the mould of FIG. 1a-b in the closed position and FIG. 4 shows a top view of a schematically represented mould with three cross slides.
Figure 3B:
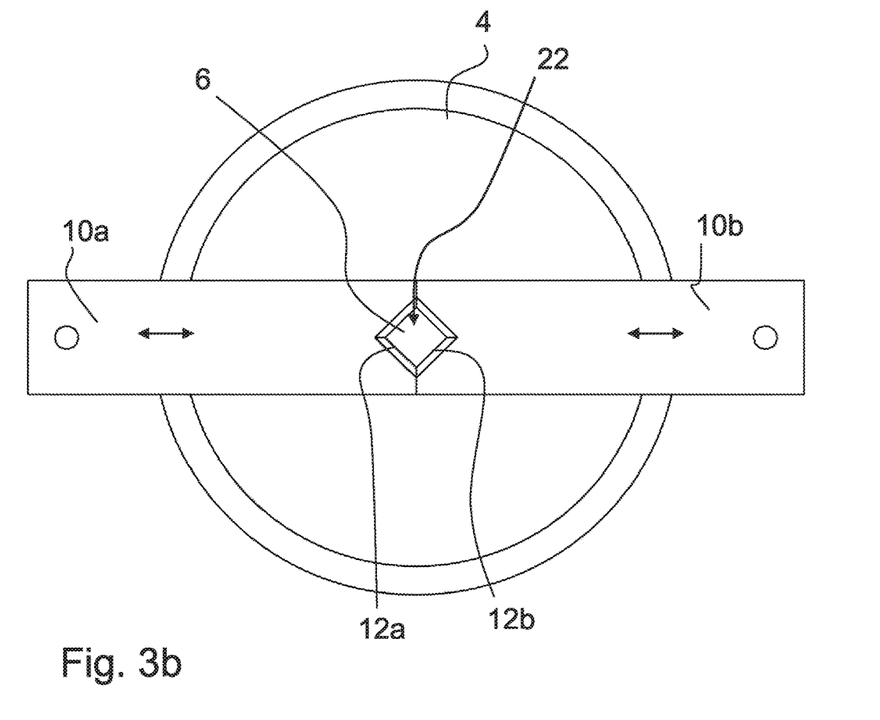

FIG. 2a shows a lateral sectioned view of the open mould 2. The upper punch 8 is guided in an upper die region 16 in the charging chute 14 and the lower punch 6 is guided in a lower die region 18 in the charging chute 14. The cross slides 10a-b are arranged between the upper and lower die region 16, 18 and are guided in recesses or openings of the die 4 such that they are displaceable in the (transverse) direction B, radially with respect to the press axis A. The cross slides are shown in the open position or moved apart from one another in FIG. 1a and FIG. 2a-b. In FIG. 1b and FIG. 3a-b the cross slides 10a-b are shown in their respective end position or in the closed position.

FIG. 3a shows a lateral sectioned view of the (closed) mould 2. A mould cavity 22, which establishes the shape or outside contour of a green compact to be pressed (not shown), is determined by forming faces 12a-b on the cross slides 10a-b and the punch faces (the bottom surface of the upper punch 8 and the top surface of the lower punch 6) of the two punches 6, 8. The die 4 does not comprise any forming faces which determine the outside contour of a green compact to be pressed.

Each cross slide 10a-b comprises a forming face 20a-b, the forming faces 12a-b of both or all cross slides 10a-b establishing the entire lateral outside contour of a green compact. As can be seen in FIG. 1a and FIG. 2b, the cross slides 10a-b are wider than the contour (in top view) of a green compact to be pressed such that each cross slide 10a-b comprises in each case a contact face 20a-d on both sides of its forming face. The contact faces 20a-d of the adjacent cross slides 10a-b abut against one another when both cross slides 10a-b are arranged in their end position (FIG. 1a and FIG. 3a-b). The wide contact faces 20a-d ensure that the mould cavity 22 is securely surrounded by the cross slides 10a-b.

With the above-described mould 2 the pressing region or the form-giving region, which is established by the cross slides 10a-b and the upper and lower punch 6, 8, is separated from the powder charging region or from the die 4. As a result of the functional separation between then pressing region and the powder charging region, individual form-giving elements, for example, such as the cross slides 10a-b can be exchanged or replaced in a simple manner without the die 4 having to be replaced. If, for example, the lateral outside contour of a green compact is to be modified or the form-giving face (on one or several cross slides 10a-b) is worn, simply one or several of the cross slides 10a-b have to be exchanged.

Producing a green compact with the above-described mould 2 is described below as an example.

First of all the mould is prepared in the open position (FIG. 2a). In a first step the two cross slides 10a-b are moved into their end position such that their contact faces 20a-d contact one another. The contact faces 20a-d only contact one another in the end position, in particular the faces 12a-d do not slide along on one another such that it is ensured that no wear is generated between the contact faces 20a-d which could impair the faces 20a-d abutting tightly against one another.

When the cross slides 10a-b are in the end position, powder material is filled (from above) into the charging chute 14. The powder material is then compacted as a result of moving the upper and lower punch 8, 6 in the direction of the press axis A until the punches 6, 8 also reach their end position, as shown in FIG. 3a.

The green compact pressed from the powder material can be ejected out of the mould 2 by the two cross slides initially being moved away from the green compact 10a-b. In said development the cross slides 10a-b are moved radially outward into the open position. The green compact which is clamped between the upper and lower punches 8, 6 can then be moved out of the die 4 or out of the charging chute 14 as a result of moving both punches 6, 8 upward or downward. The green compact can then be gripped, for example, by means of a gripping device and after moving both or just one of the punches 6, 8 can be forwarded by means of the gripping device. For example, directly to the sintering process or to a process for machining the green compact prior to sintering.

In order to ensure a fault-free pressing operation, bores (not shown) can be provided in the die 4 for cleaning purposes, through which bores a flushing medium (e.g. compressed air) is conducted in order, for example, to clean the forming faces 12a-b, the contact faces 20a-d and/or the guide faces for the cross slides 10a-b of powder residue. As an alternative to this or in addition to it, brushes can be guided through bores in the die 4 up to the named faces in order to clean the faces. A further development for cleaning the mould 2, in addition to or as an alternative to the abovementioned developments, includes a suction device in order to suck up (released) powder residue out of the mould 2.

Figure 4:
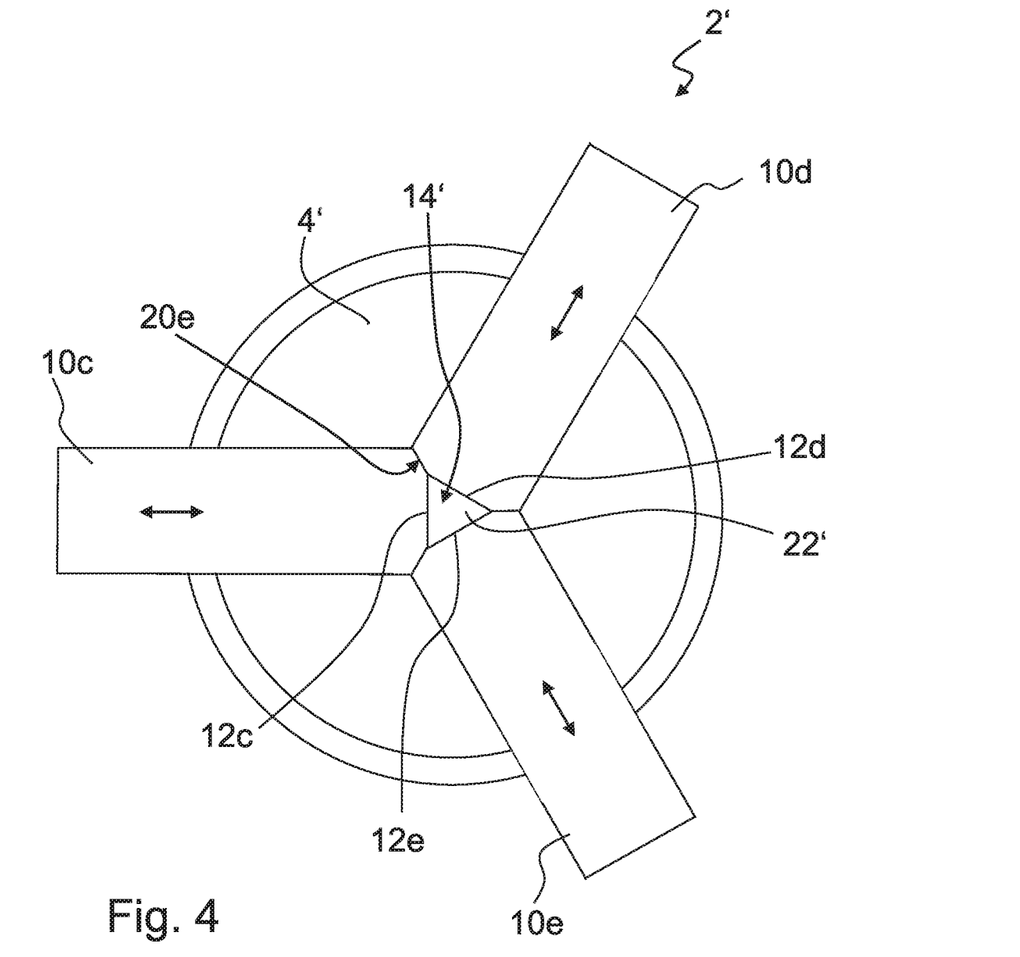

FIG. 4 shows a top view of a schematic representation of a mould according to a further development. The same and similar elements comprise the same and similar references. Insofar as nothing to the contrary is stated, the elements and the use of the development of the mould 2' described below correspond to the elements and the use of the development of the mould 2 described above.

In contrast to the above development, the mould shown in FIG. 4 comprises three cross slides 10c-e which are arranged uniformly around the press axis or around the die 4' with the charging chute 14'. The cross slides 10c-e are shown arranged in the closed position or in the end position and enclose a mould cavity 22' with a triangular footprint. In order to show the arrangement of the three cross slides 10c-e, an upper die region and the upper punch of the mould 2' have been omitted.

The cross slides 10c-e are mounted so as to be radial movable in openings of the die 4'. Each of the cross slides 10c-e comprises a forming face 12c-e auf, all the forming faces 12c-e of the cross slides 10c-e together establishing the entire lateral outside contour of the mould cavity 22' or of a green compact. As described above, the die 4' does not comprise any forming faces which determine the outside contour of a green compact.

A contact face 20e between two adjacent cross slides 10c, 10e is marked as an example. The contact faces 20e of the cross slides 10c-e which are arranged laterally to the forming faces 12c-e only come into contact when the adjacent cross slides 10c-e are arranged in the end position or the closed position. An angle between the radial direction of movement of the cross slides, e.g. cross slide 10c, and the associated contact face 20e is 60° . In the case of the development shown above in FIG. 1a-b, the angle between the direction of movement of a cross slide 10a-c and its corresponding contact face 20a-d is 90°. If, for example, a mould is provided with four cross slides which are distributed uniformly around the press axis, the above-mentioned angle would then be 45°.

LIST OF REFERENCES 2, 2' mould
4, 4' die
6 lower punch
8 upper punch
10a-e cross slide
12a-e forming face cross slide/outside contour
14, 14' charging chute
16 upper die region
18 lower die region
20a-e contact face
22, 22' mould cavity
A press axis

The invention claimed is:

1. A mold for producing a green compact using powder metallurgy processes, the mold comprising:
   an upper punch and a lower punch being movable along a common press axis;
   a die body having a charging chute formed therein for receiving powder material, said die body having an upper die region in which said upper punch is movably guided along the common press axis in said charging chute and a lower die region in which said lower punch is movably guided along the common press axis in said charging chute; and
   at least two cross slides which realize a forming region which determines a lateral outside contour of the green compact, and disposed on said die body so as to be displaceable in a direction which deviates from the common press axis, said at least two cross slides only move into contact with one another when said at least two cross slides are disposed in their respective end position and a cavity, for determining a shape of a pressed green compact, is realized in a closed state of the mold by said lower and upper punches which are disposed in end positions and by said at least two cross slides which are disposed in the end positions, said at least two cross slides realize the forming region which determines an entire lateral outside contour of the green compact.

2. The mold according to claim 1, wherein said upper die region and said lower die region are free of portions which determine an outside contour of the green compact.

3. The mold according to claim 1, wherein an extension of said at least two cross slides in the direction of the common press axis corresponds to an extension of the green compact in the direction of the common press axis.

4. The mold according to claim 1, wherein:
   said upper die region engages around said upper punch completely in a circumferential direction; and/or
   said lower die region engages around said lower punch completely in the circumferential direction.

5. The mold according to claim 1, wherein said upper die region and said lower die region are realized in one piece or are connected together in a non-releasable manner.

6. The mold according to claim 1, wherein:
   each of said cross slides projects laterally beyond said cavity; or
   each of said cross slides projects laterally beyond an outside contour of the green compact to be pressed.

7. The mold according to claim 1, wherein:
   each of said at least two cross slides has forming portions;
   each of said at least two cross slides has two contact faces which are disposed laterally with respect to one of said forming portions of a cross slide; and
   said contact faces of adjacent said cross slides only contact one another when said at least two cross slides are disposed in the end positions.

8. The mold according to claim 7, wherein an angle between a direction of displacement of said cross slide and one of said contact faces of said cross slide is at least 40°.

9. The mold according to claim 7, wherein an angle between a direction of displacement of said cross slide and one of said contact faces of said cross slide is between 45° and 90°.

10. A method for producing a powder-metallurgy component, which comprises the steps of:
    providing a mold for producing a green compact, the mold comprising:
       an upper punch and a lower punch being movable along a common press axis;
       a die body having a charging chute formed therein for receiving powder material, the die body having an upper die region in which the upper punch is movably guided along the common press axis in the charging chute and a lower die region in which the lower punch is movably guided along the common press axis in the charging chute; and
       at least two cross slides which realize a forming region which determines a lateral outside contour of the green compact, and disposed on the die body so as to be displaceable in a direction which deviates from the common press axis, the at least two cross slides only move into contact with one another when the at least two cross slides are disposed in their respective end position and a cavity, for determining a shape of a pressed green compact, is realized in a closed state of the mold by the lower and upper punches which are disposed in end positions and by the at least two cross slides which are disposed in the end positions, the at least two cross slides realize the forming region which determines an entire lateral outside contour of the green compact;

pressing the green compact out of the powder material using the mold; and sintering the green compact to form a sintered component.

11. The method according to claim 9, wherein the pressing step further comprises the following steps of:

preparing the mold by disposing the upper punch, the lower punch and the at least two cross slides in an open position;

moving the at least two cross slides into the end positions such that when the end positions are reached contact faces of adjacent ones of the cross slides abut against one another, the at least two cross slides in the end positions realize the forming region for the entire lateral outside contour of the green compact to be pressed;

filling the powder material into the charging chute of the die body; and moving at least one of the upper punch or the lower punch along the common press axis up to the end position of at least one of the upper punch or to the end position of the lower punch.

12. A production method, which comprises the steps of:

providing a mold for producing the green compact, the mold comprising:

an upper punch and a lower punch being movable along a common press axis;

a die body having a charging chute formed therein for receiving powder material, the die body having an upper die region in which the upper punch is movably guided along the common press axis in the charging chute and a lower die region in which the lower punch is movably guided along the common press axis in the charging chute; and at least two cross slides which realize a forming region which determines a lateral outside contour of the green compact, and disposed on the die body so as to be displaceable in a direction which deviates from the common press axis, the at least two cross slides only move into contact with one another when the at least two cross slides are disposed in a respective end position and a cavity, for determining a shape of a pressed green compact, is realized in a closed state of the mold by the lower and upper punches which are disposed in end positions and by the at least two cross slides which are disposed in the end positions, the at least two cross slides realize the forming region which determines an entire lateral outside contour of the green compact; and producing a cutting insert for machining a work piece by means of powder metallurgy and the mold.

* * * * *